(12) United States Patent
Wheeler et al.

(10) Patent No.: US 8,047,407 B2
(45) Date of Patent: Nov. 1, 2011

(54) APPARATUS AND METHOD FOR DELIVERY OF BIOLOGIC SEALANT

(75) Inventors: John L. Wheeler, Austin, TX (US); Gary Whipple, Attleboro, MA (US); A. David Boccuti, Arlington, MA (US); Thomas T. Washburn, Concord, MA (US); Andrew Nicholas Gentile, Waltham, MA (US); J. Brent Ratz, Winchester, MA (US); John Spiridigliozzi, San Mateo, CA (US)

(73) Assignee: Spinal Restoration, Inc., Austin, TX (US)

( * ) Notice: Subject to any disclaimer, the term of this patent is extended or adjusted under 35 U.S.C. 154(b) by 107 days.

(21) Appl. No.: 11/977,441

(22) Filed: Oct. 24, 2007

(65) Prior Publication Data

US 2008/0060970 A1    Mar. 13, 2008

Related U.S. Application Data

(63) Continuation-in-part of application No. 11/205,784, filed on Aug. 17, 2005, and a continuation-in-part of application No. 11/205,775, filed on Aug. 17, 2005, now Pat. No. 7,597,687, and a continuation-in-part of application No. 11/205,760, filed on Aug. 17, 2005.

(60) Provisional application No. 60/854,413, filed on Oct. 24, 2006, provisional application No. 60/623,600, filed on Oct. 29, 2004, provisional application No. 60/764,019, filed on Feb. 1, 2006, provisional application No. 60/764,020, filed on Feb. 1, 2006.

(51) Int. Cl.
  *B65D 88/54* (2006.01)

(52) U.S. Cl. .............. 222/287; 604/48; 604/61; 604/71; 604/173; 604/187; 604/191; 604/223; 604/233; 604/287; 222/255; 222/280; 222/281

(58) Field of Classification Search .................. 222/255, 222/280, 281, 287; 604/48, 61, 71, 173, 604/187, 191, 223, 233, 281, 287
See application file for complete search history.

(56) References Cited

U.S. PATENT DOCUMENTS 3,117,696 A * 1/1964 Herman et al. ................ 222/137
3,223,083 A * 12/1965 Cobey ............................. 606/92

(Continued)

OTHER PUBLICATIONS

PCT/US2007/022533, "*International Search Report*," Oct. 24, 2007.

*Primary Examiner* — Nicholas D Lucchesi
*Assistant Examiner* — Scott Medway
(74) *Attorney, Agent, or Firm* — O'Keefe, Egan, Peterman & Enders, LLP

(57) ABSTRACT

A device for delivery of biologic materials, comprising: a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams, as well as methods of making the device, methods of using the device to treat discs, kits including the device.

27 Claims, 12 Drawing Sheets

U.S. PATENT DOCUMENTS

| | | | |
|---|---|---|---|
| 3,390,814 A * | 7/1968 | Creighton, Jr. et al. | 222/137 |
| 4,264,305 A * | 4/1981 | Rasmussen et al. | 433/90 |
| 4,447,223 A * | 5/1984 | Kaye et al. | 604/61 |
| 4,471,888 A * | 9/1984 | Herb et al. | 222/137 |
| 4,669,636 A * | 6/1987 | Miyata | 222/153.01 |
| 4,978,336 A * | 12/1990 | Capozzi et al. | 604/82 |
| 4,998,570 A * | 3/1991 | Strong | 141/27 |
| 5,064,098 A * | 11/1991 | Hutter et al. | 222/137 |
| 5,080,648 A * | 1/1992 | D'Antonio | 604/72 |
| 5,295,614 A * | 3/1994 | Chang | 222/137 |
| 5,520,658 A * | 5/1996 | Holm | 604/191 |
| 5,582,596 A * | 12/1996 | Fukunaga et al. | 604/191 |
| 5,865,804 A * | 2/1999 | Bachynsky | 604/134 |
| 5,989,215 A * | 11/1999 | Delmotte et al. | 604/82 |
| 6,007,515 A * | 12/1999 | Epstein et al. | 604/82 |
| 6,126,682 A * | 10/2000 | Sharkey et al. | 607/96 |
| 6,132,396 A | 10/2000 | Antanavich et al. | 604/82 |
| 6,387,977 B1 | 5/2002 | Sawhney et al. | 522/184 |
| 6,461,325 B1 * | 10/2002 | Delmotte et al. | 604/82 |
| 6,471,667 B1 * | 10/2002 | Epstein | 604/28 |
| 6,599,272 B1 | 7/2003 | Hjertman et al. | 604/209 |
| 7,306,587 B2 * | 12/2007 | O'Sullivan et al. | 606/1 |
| 2002/0170926 A1 * | 11/2002 | Horner et al. | 222/137 |
| 2006/0106364 A1 | 5/2006 | Whitlock et al. | 604/506 |

* cited by examiner

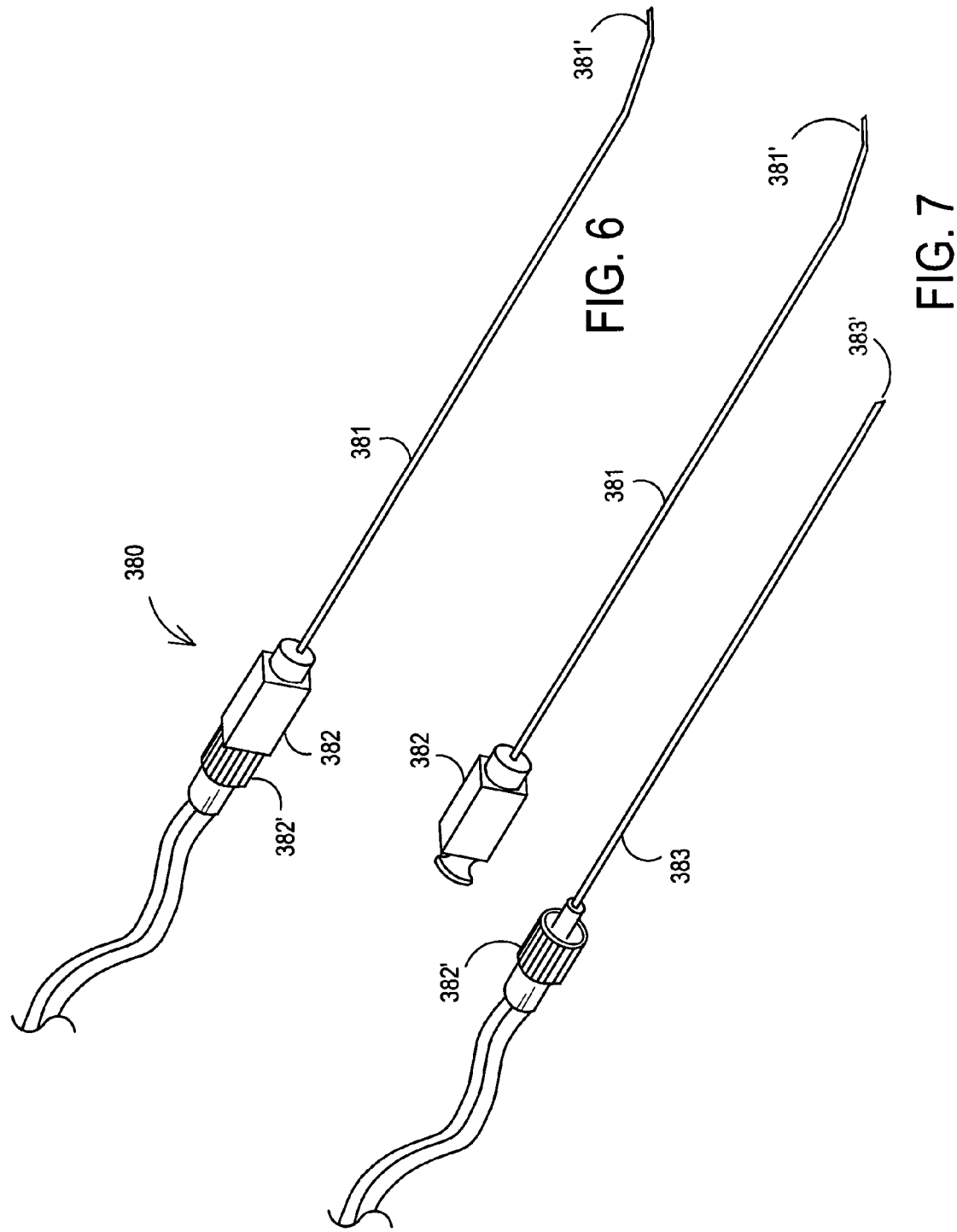

APPARATUS AND METHOD FOR DELIVERY OF BIOLOGIC SEALANT

This application claims priority to U.S. provisional application No. 60/854,413, filed Oct. 24, 2006, to U.S. provisional application No. 60/623,600, filed Oct. 29, 2004 and is a continuation-in-part of U.S. application Ser. No. 11/205,760, filed Aug. 17, 2005, of U.S. application Ser. No. 11/205,784, filed Aug. 17, 2005, and of U.S. application Ser. No. 11/205,775, filed Aug. 17, 2005 now U.S. Pat. No. 7,597,687, and this application claims priority to U.S. provisional application No. 60/764,019, filed Feb. 1, 2006, and this application claims priority to U.S. provisional application No. 60/764,020, filed Feb. 1, 2006, all of which are incorporated herein by reference.

FIELD OF THE INVENTION

The disclosure herein generally relates to an apparatus and method for the delivery of a biologic sealant such as fibrin sealant.

BACKGROUND OF THE INVENTION

Fibrin sealants, and glues, are well known and are used extensively in various clinical settings. Such sealants are indicated as adjuncts to hemostasis in surgeries when control of bleeding by conventional surgical techniques, including suture, ligature, and cautery is ineffective or impractical. In these cases, the sealant was applied topically. Delivery devices have been developed for these uses. Typical fibrin sealant devices are adapted to spray the fibrin sealant.

More recently, fibrin sealant has been used to treat degenerative disc disease that leads to discogenic pain. In this regard, U.S. Pat. No. 6,468,527 (Austin) discloses the injection of a fibrin sealant into the intra-discal space. This patent discloses use of a dual syringe system wherein thrombin and fibrinogen initially mix in a Y-connector that attaches to a needle and to the two syringes. The fibrin sealant immediately begins clotting upon contact of the fibrinogen and the thrombin. The components continue to mix and clot as they travel down the spinal needle toward the tip of the needle that is in the disc.

However, the inventors herein have recognized that the prior delivery device shown in U.S. Pat. No. 6,468,527 is prone to clogging due to clotting of the components within the needle. In addition, the inventors have recognized that it would be desirable for a surgeon administering the sealant to know the pressure of the components being delivered so that the surgeon does not over-pressurize the disc and/or so that the surgeon can use the delivery device as a diagnostic tool to ascertain the extent of damage to the disc.

SUMMARY OF THE INVENTION

This invention provides a solution to one or more of the disadvantages and desired capabilities described above.

In the practice of the present invention, a biologic sealant such as fibrin sealant can be introduced into, for example, the spinal area of a human being. Fibrin sealant comprises fibrinogen and thrombin, which form fibrin when mixed. Calcium chloride may be included in the fibrin sealant. The fibrin may optionally include one or more additives, such as various biological and non-biological agents.

In one broad respect, this invention is an apparatus for delivery of a biologic sealant. This device comprises a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

In another broad respect, this invention is a method of making a device for delivery of biologic materials, comprising: providing a cartridge having at least two cylinder bores for fluids to be delivered, wherein each cylinder includes an exit port for a fluid, providing a plunger within each cylinder for pushing the fluids out of the cylinder, providing a housing adapted to receive the cartridge, wherein the housing or cartridge includes an adaptor to receive and lock a manifold that operably connects to the exit ports of the cartridge, providing at least two toothed rams, wherein each toothed ram is at least partially within a cylinder bore, providing a trigger connected to the housing, wherein the trigger includes a toothed drive rack, providing a toothed wheel assembly that cooperates with the toothed drive rack and with the toothed rams.

In another broad respect, this invention is a kit for treating a disc, comprising: fibrinogen, thrombin, and a device for delivery of biologic materials, wherein the device comprises: a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

In another broad respect, this invention is a method of making a kit, comprising providing fibrinogen, providing thrombin, and providing a device for delivery of biologic materials, wherein the device comprises: a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

In another broad respect, this invention is a method of treating a disc that is leaking nucleus pulposus through at least one defect in the annulus fibrosus, comprising: injecting a fibrin sealant or other biologic sealant into the disc to reduce at least a portion of the at least one defect, wherein the fibrin sealant injected into the disc comprises fibrinogen and thrombin, wherein the fibrin sealant is injected using a delivery device that comprises: a cartridge having at least two cylinder bores for fluids to be delivered, wherein each cylinder includes an exit port for a fluid, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams. The defect can be a tear of the annulus fibrosus, a fissure in the annulus fibrosus, and the like. Advantageously, injection of the fibrin sealant can also serve to restore normal hydrostatic pressure, a key component to disc health.

In certain embodiments of the device, kit, and methods of this invention, the housing and the cartridge are together monolithic; the cartridge is a separate component from the housing that is inserted into the housing; the device includes a pressure manometer operably connected to measure the pressure in at least one cylinder; wherein the plungers are attached to the rams; the wheel assembly includes an inner toothed wheel sandwiched between two outer toothed wheels each of smaller diameter than the inner wheel; the drive rack engages the wheel assembly upon manual pressure to the trigger and wherein the drive rack disengages the wheel assembly upon release of pressure on the trigger, and falls away; the device includes a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor; the device includes a delivery manifold for delivering the fluids, comprising a delivery adaptor that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fitting; the luer fitting is configured to deliver fluid from one conduit to an inner needle and wherein the luer fitting is configured to deliver fluid from the second conduit to a space defined by the exterior of the inner needle and by a second larger diameter needle that connects to the luer fitting with the inner needle being within the inside of the larger diameter needle, especially where the tip of the inner needle extends up from about 1.5 inch to about 0.5 inch from the distal tip of the outer needle and in one embodiment is from about 0.75 inch to about 1 inch from the distal tip, especially where the inner needle is an 18 gauge needle and the outer needle is a 22 gauge needle; and combinations thereof.

In one embodiment, in the practice of this invention the nucleus pulposus has not been removed by surgery, such as in the case of a total or partial discectomy or by nucleoplasty for a herniated disc.

This invention also includes a kit including the delivery device of this invention and the components used to inject the fibrin sealant. The components may comprise fibrinogen, such as freeze-dried fibrinogen, thrombin such as freeze-dried thrombin, and the delivery device. The kit can optionally include CaCl, contrast agent and other additives.

Advantageously, the device, methods, and kit of this invention facilitate extended pain relief for patients with discogenic pain, wherein for example nucleus pulposus leaks out of the disc through defects (e.g. tears or fissures) in the annulus fibrosus. Surprisingly, it has been found that the device of this invention which employs an outer introducer needle and an inner needle within the introducer needle, wherein the tip of the inner needle does not protrude past the distal tip of the outer introducer needle, and in one embodiment is approximately one inch from the distal tip of the outer introducer needle, provides a final fibrin sealant clot with surprising properties. This needle configuration facilitates mixing of the components of the fibrin sealant (or other biologic sealant) to provide improved set-up time (or "work time"), less viscosity with slower set up to afford easier use in practice and higher penetration of sealant into tears, fissures, and so forth, enhanced mechanical properties of the final sealant including greater elasticity (easier to deform) with slightly less failure load (i.e., the force required to make a permanent rupture), approximately a 200% improvement in fracture toughness (i.e., need twice as much energy to break the sealant as compared to a clot made using a standard device), extended solidification time of about twice as long to reach 10,000 poise viscosity, with the ultimate sealant having sufficient mechanical properties to be useful for intradiscal injections. Likewise, the device of this invention advantageously allows a practitioner to reuse the delivery gun in a sterile environment for multiple injections for a patient by removing the injection manifold, loading the cartridges with fresh sealant components, attaching the same or new injection manifold, inserting a second or the same introducer needle intradiscally, inserting the inner needle within the introducer needle, and applying pressure to the trigger to inject sealant. The device should be primed with sealant components prior to insertion of the inner needle. Likewise, by use of the device of this invention, where the inner needle does not extend past the distal tip of the outer needle, and where the tip of the inner needle is within an inch or two inches from the distal tip of the longer outer needle, it has been found that partially set up sealant within the needles can be readily pushed out of the needles to thereby advantageously clear (unclog) the needles for delivery of additional sealant, which begins mixing at the tip of the inner needle.

BRIEF DESCRIPTION OF THE DRAWINGS

FIGS. 6-8 show one embodiment of the needle assembly of this invention.

DETAILED DESCRIPTION OF THE INVENTION

The delivery device of this invention is illustrated in the figures. In general, the device of this invention comprises: a cartridge having at least two cylinder bores for fluids to be delivered, wherein each cylinder includes an exit port for fluid, a plunger within each cylinder for pushing fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

Figure 1:
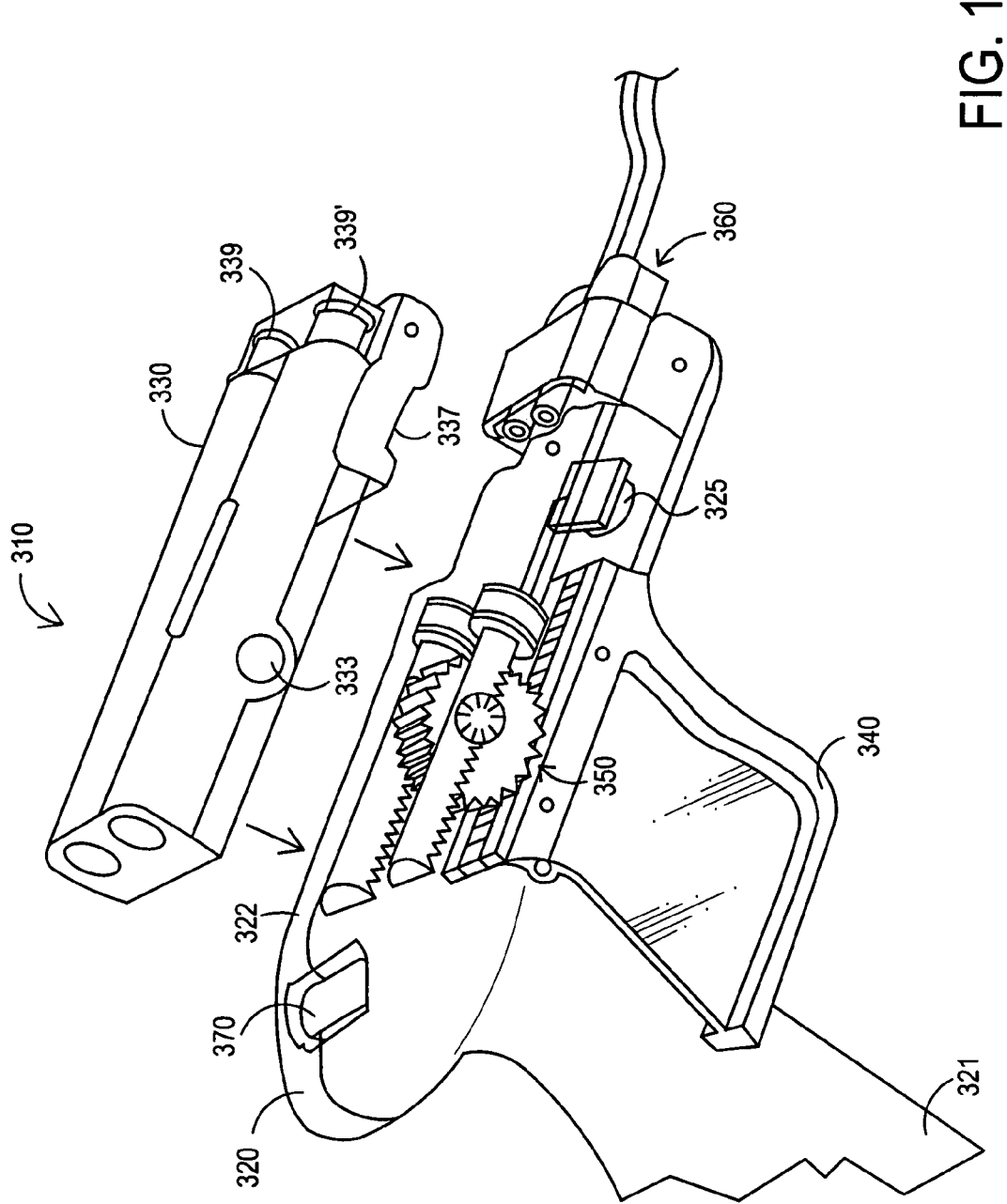
FIG. 1 shows a semi-exploded view of one embodiment of the device of this invention.

Referring now to FIG. 1, a representative delivery device of this invention is depicted. The device 10 includes a housing 20 that holds or is connected to some of the device's other parts. The housing can be made from a variety of materials, but is typically made from one or more plastic materials. The housing can generally be referred to as being in the shape of a pistol or gun, including a handle 21 and barrel 22. A cartridge 30 is positioned within the barrel 22. The housing is adapted to receive and house the cartridge. The cartridge 30 is thus positioned within the barrel 22. The housing can be a multi-piece component, such as a two piece housing that is assembled using screws, or configured using snap-in type functionality. The specific design shown in FIG. 1 is merely representative and not intended to limit the types of housings employed in the practice of this invention.

In addition, a trigger 40 is operably connected to and situated within the housing so that the trigger 40 can slide from a first position into the housing to a second position as pressure is applied by the operator to the trigger 30. The housing 20 can include an internal stop, not shown, for the travel of the trigger 30.

Figure 2:
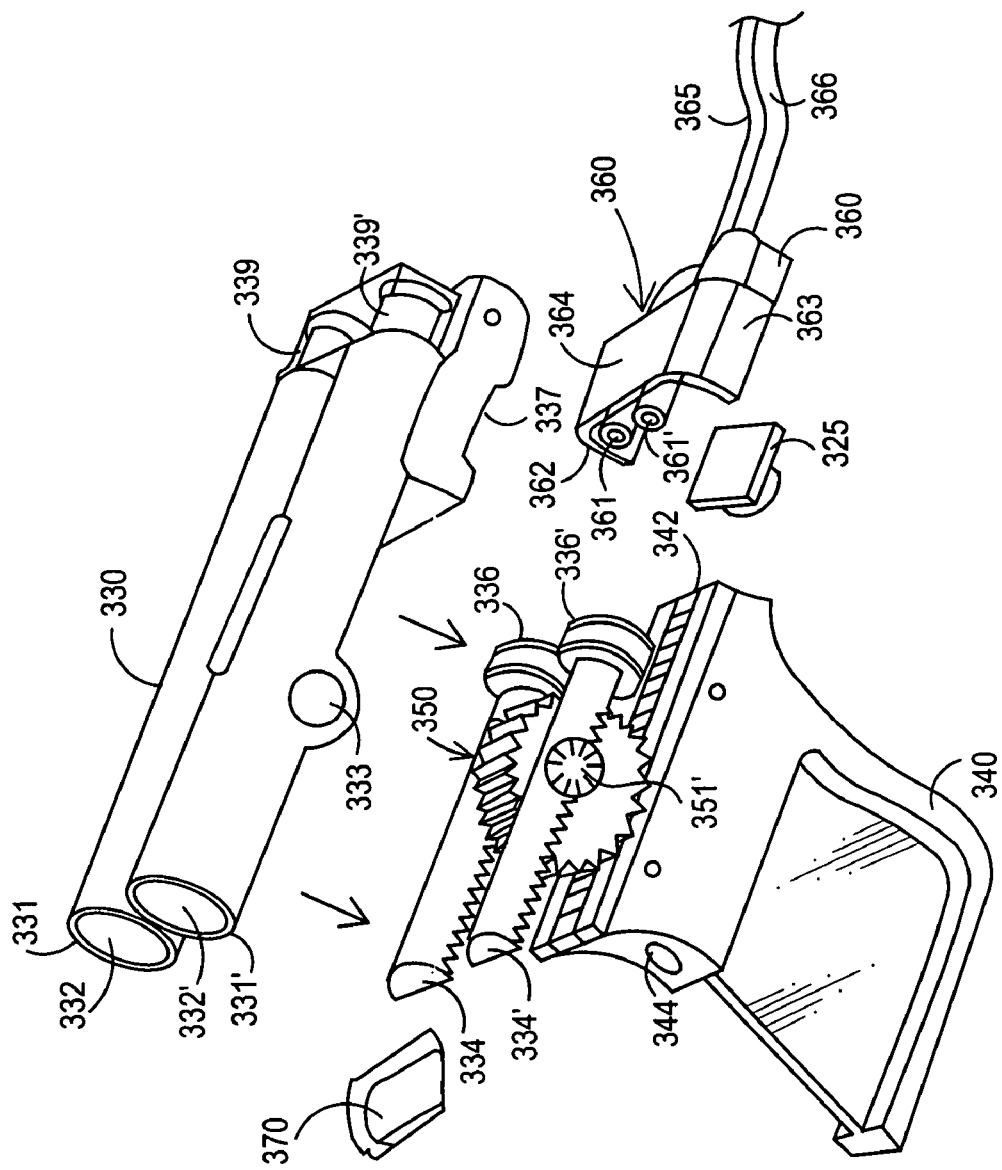
FIG. 2 shows a semi-exploded view of components of one embodiment of the device of this invention.
Figure 3:
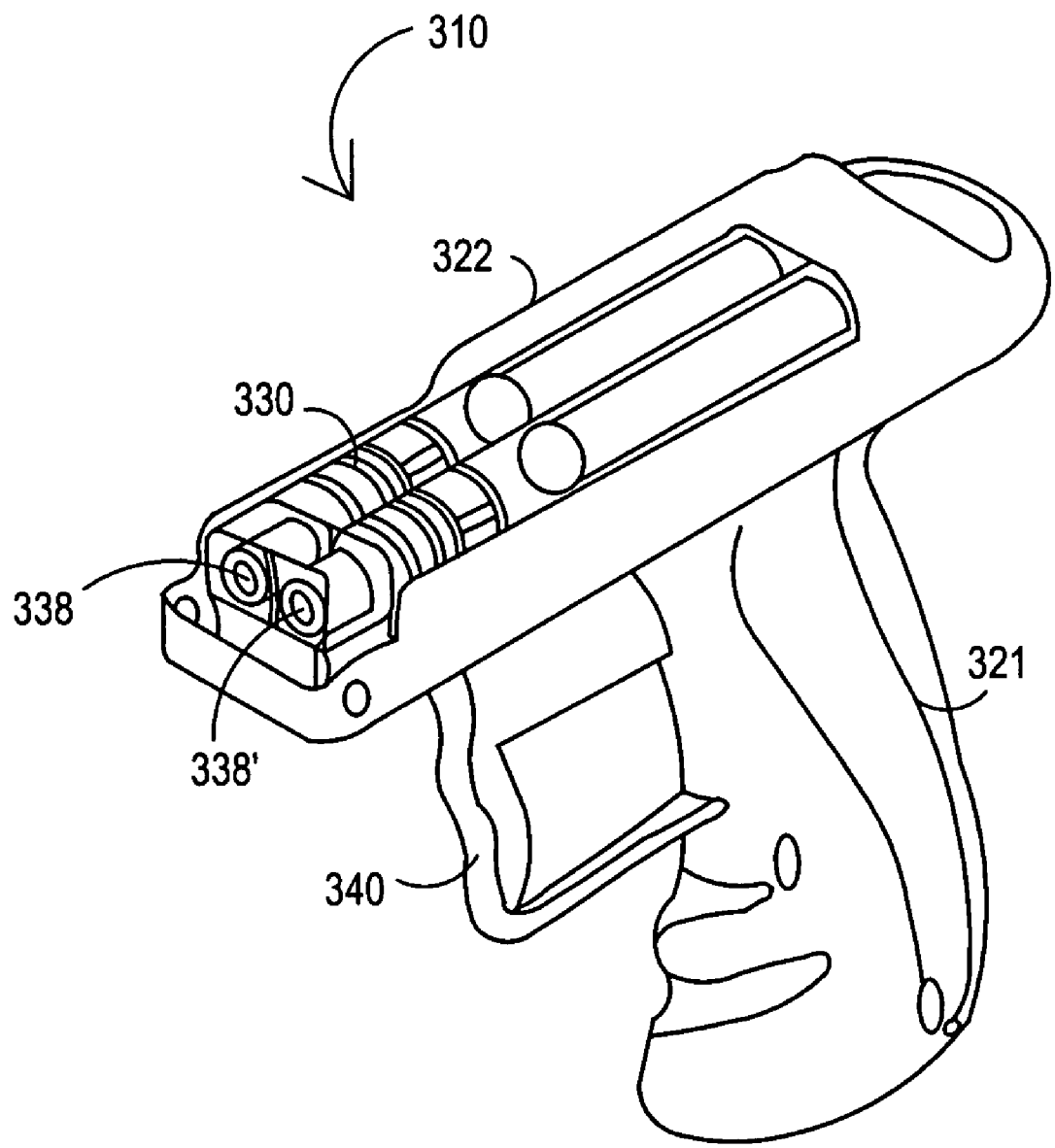
FIG. 3 shows a device of this invention, including exit ports 38, 38' of the cartridge 30.
Figure 4:
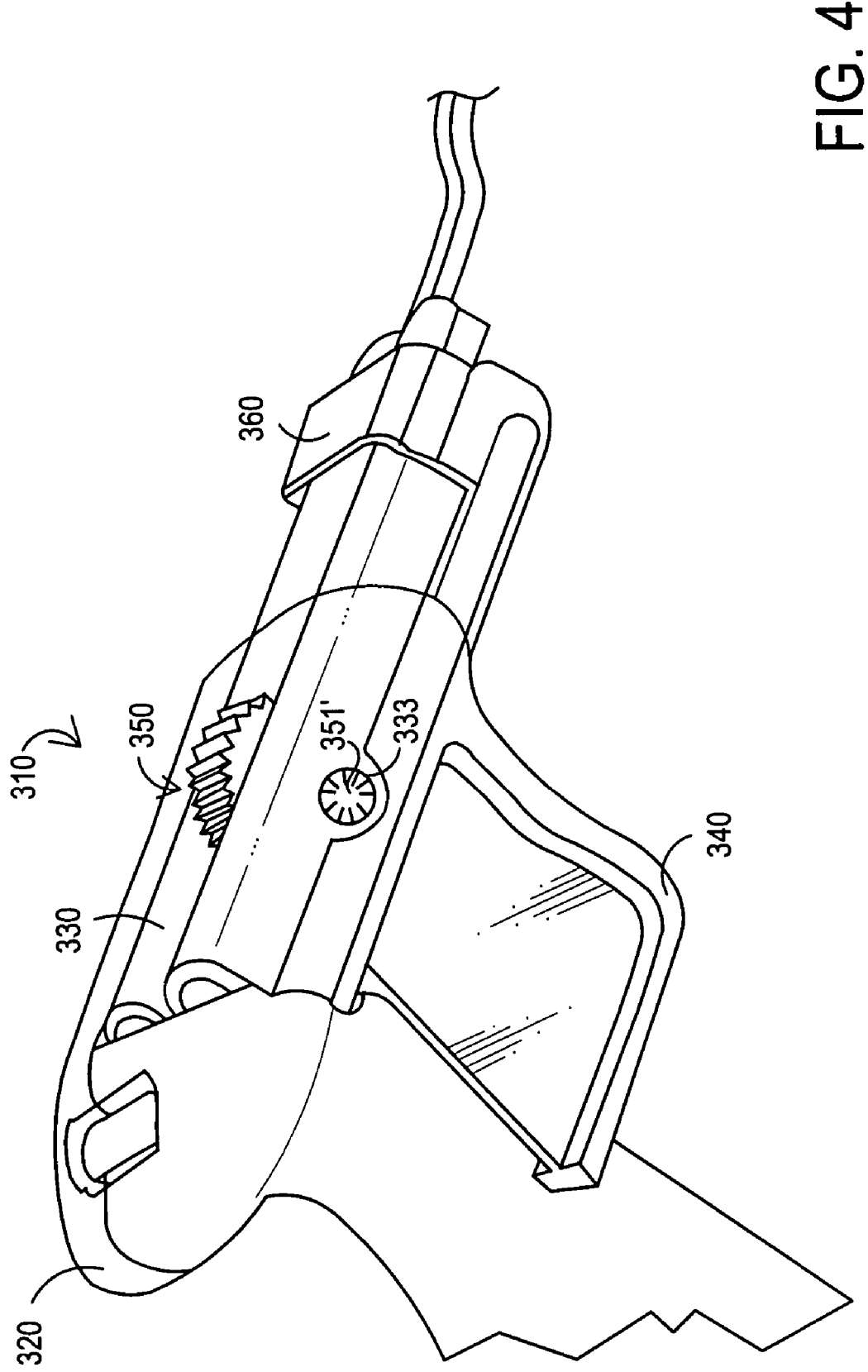
FIG. 4 shows a perspective view of the device of this invention.

The cartridge 30 is depicted in greater detail in FIG. 2. Thus, the cartridge 30 includes two cylinders 31, 31' that each has a bore 32, 32' for receipt of a fluid. Each cylinder 31, 31' defines a generally straight tube having the same diameter for the length of the bores 32, 32'. The cartridge 30 may include one or more fittings, slots, or the like that serve to secure the cartridge 30 within the housing. For example in FIG. 2 the housing includes a fitting 53 that is configured to fit within slot 37 of the cartridge to thereby secure cartridge 30 from lateral movement. It should be appreciated that the cartridge 30 does not move upon application of pressure to the trigger 40. Rather, application of pressure to the trigger 40 engages the rack 42, wheel assembly 50, and rams 34, 34' to push the plungers 36, 36' toward the exit ports 38, 38' (see FIG. 3) of the cartridge 30. In FIG. 2, the extended gear ends 51, 51' of the wheel assembly 50 fit into bore 33 of the cartridge 30 (see also FIG. 4). It should be appreciated that the cartridge 30 can be integral with the housing 20. That is, the cartridge 30 need not be a separate and/or detachable component that is placed within the housing but instead can be formed as part of the housing during fabrication of the housing. Likewise, the cartridge can be of one-piece or multi-piece construction. In the figures the cartridge 30 is one-piece.

Figure 5:
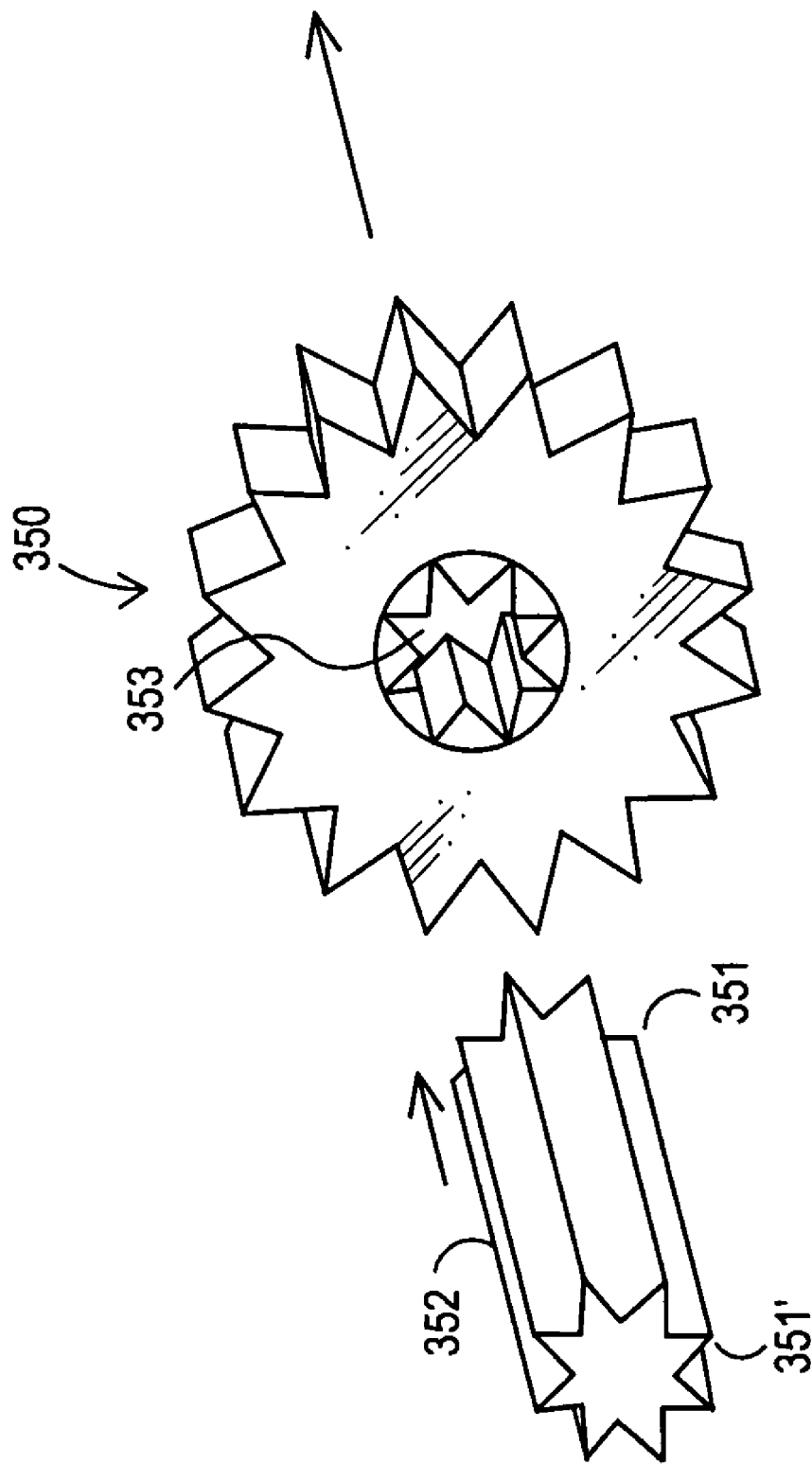
FIG. 5 shows a wheel assembly used in one embodiment of the device of this invention.

It should be appreciated that the wheel assembly 50 can be a single piece or can be assembled from multiple parts to form the assembly. Thus, for example, with respect to a multiple-part assembly, as depicted in FIG. 5, a toothed internal gear 52 having extended gear ends 51, 51' is inserted into internal bore 53 of wheel 50. The gear 52 is adapted to engage the wheel 50, such as by interdigitating teeth, so that the assembly would move as a single part during use of the device 10. In this embodiment, the inner toothed gear 52 can be seen to be sandwiched between the extended gear ends 51, 51. Alternatively, the wheel assembly can be cast, forged, milled, or otherwise formed to manufacture a single monolithic wheel assembly. Alternatively to teeth, the wheel assembly 50, rack 42, and rams can be made of materials that engage with sufficient friction to provide the desired movement, using for example tacky rubber materials, materials have a grainy surface (e.g., with a sand-paper like finish), and so on.

Referring again to FIG. 2, there is shown a pressure read-out display 60 that provides the surgeon with a pressure reading within one of the bores 32, 32' of the cartridge 30. A transducer, not shown, is configured to measure pressure within a bore and a line, not shown, from the transducer to the display 70 provides a signal to electronic circuitry that processes the signal and provides a reading to display 70. Thus, the pressure monitor couples to the delivery device through a line connected to a transducer in, for example, one of the syringes. Alternatively, the transducer can be located within the connector, or anywhere else where the transducer can be introduced within the device such that pressure of within the device can be measured. Preferably, the transducer is in the bore. The display can be but is not limited to an LCD.

Pressure monitors are available commercially. For example, a suitable pressure monitor is currently available from Merit Medical Systems, Inc. (Utah, US) sold as a Meritrans™ transducer. Other representative pressure monitors are disclosed in, for example, US patent application number 2005/0004518, incorporated herein by reference. In the device disclosed in 2005/0004518, a pressure transducer is integrally mounted in the plunger of a syringe under the plunger tip such that the force applied by the plunger to the fluid in the syringe is transmitted to the transducer and the resulting electronic signal is converted to a display value, aiding the physician in diagnosing diseased disks in the back. The transducer of the pressure monitor can be positioned in the barrel of a syringe or, alternatively, in the connector (or "hub").

Figure 9B:
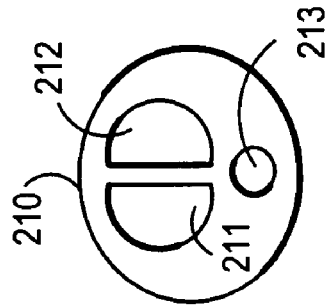
FIGS. 9A, 9B, and 9C show representative cross-sectional views of multi-lumen catheters.
Figure 9C:
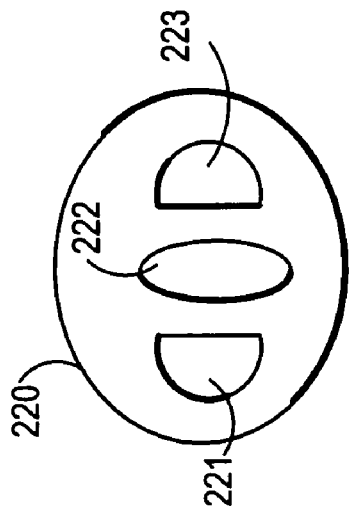
Figure 9A:
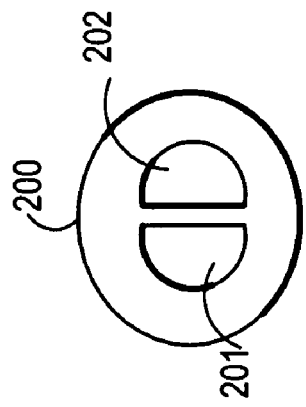
Figure 10:
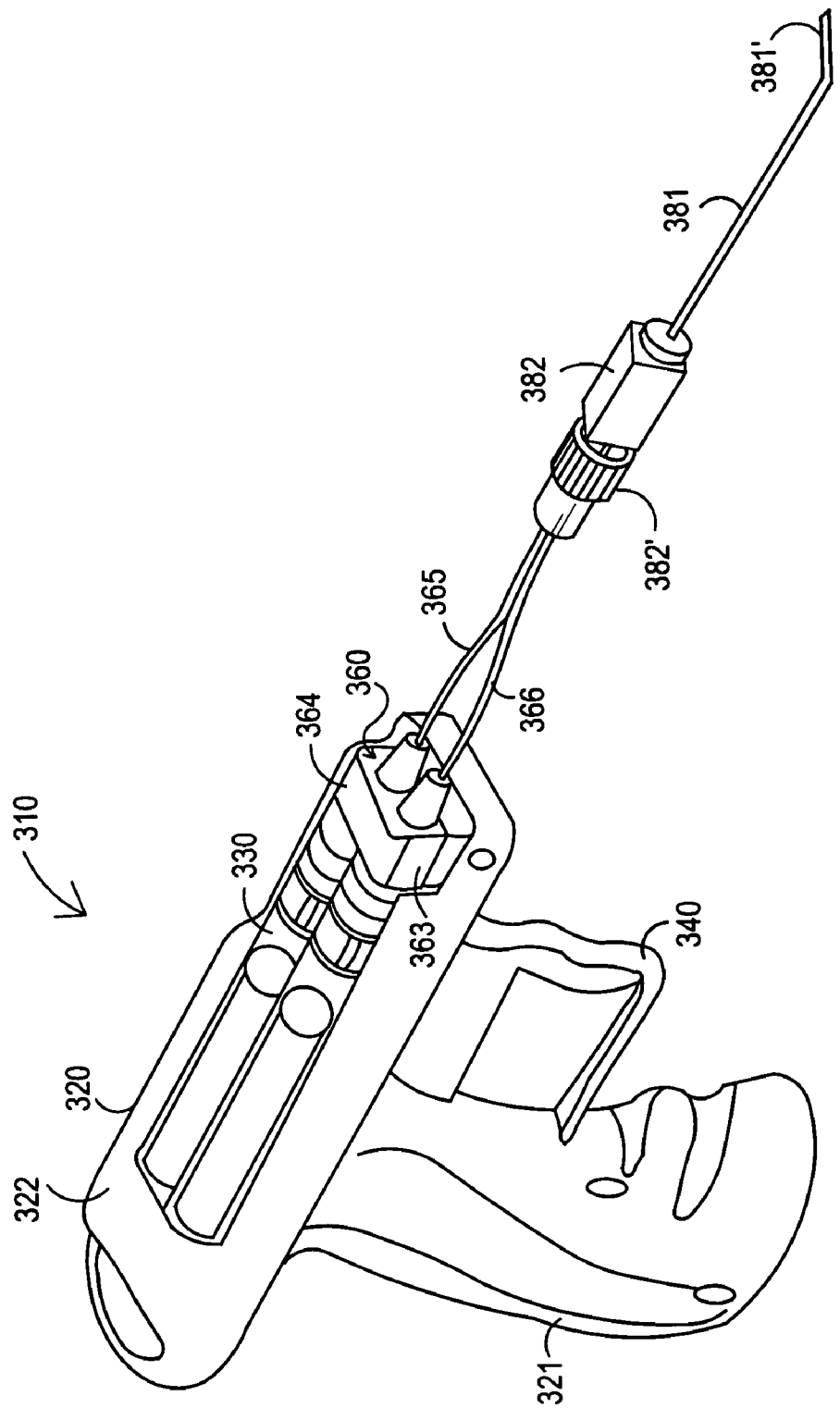
FIG. 10 shows the device of this invention with a delivery manifold operably attached to the device.

A dispenser manifold 60 is shown in FIGS. 1 and 2. The dispenser manifold 60 includes dispenser manifold inlet ports 61, 61' that sealably align and couple with the exit ports 38, 38' of the cartridge 30. The dispenser manifold 60 is adapted to couple to the manifold coupling portion 39 of the cartridge using, for example, fittings 62, 63 that engage complimentary slots 39' so as to lock in the dispenser manifold 60 to the coupling portion 39. In the embodiment depicted in the FIGS, the exit ports 38, 38' are embodied within manifold coupling portion 39. The coupling portion 39 may alternatively be formed into the housing 20, though typically is part of the cartridge 30. The dispenser manifold 60 depicted in FIGS. 1, 2, and 3 also includes an optional hood 64. The dispenser manifold 60 includes fluid tubes 65, 66 that receive and transfer fluid from the cartridge 30 to the needle assembly 80 which is depicted for example in FIGS. 6-9. The tubes 65, 66 can be made of a variety of materials, but in general are made of flexible materials to facilitate improved usage by the surgeon. Typically the tubes 65, 66 are made of polymeric materials, especially medical grade materials. Alternatively, the tubes can be made of soft metals or other materials that permit the tubes to flex. Thus the delivery manifold for delivering the fluids can include a delivery adapter that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to delivery fluid from one conduit to an inner needle and wherein the luer fitting is configured to delivery fluid from the second conduit to a space defined by the exterior of the inner needle and by a second larger diameter needle that connects to the luer fitting with the inner needle being within the insider of the larger diameter needle. FIG. 10 illustrates the device 10 where the manifold 60 has been operably connected to the cartridge 30 so that the inlet ports of the manifold 60 align with the exit ports of the cartridge 30.

Figure 11:
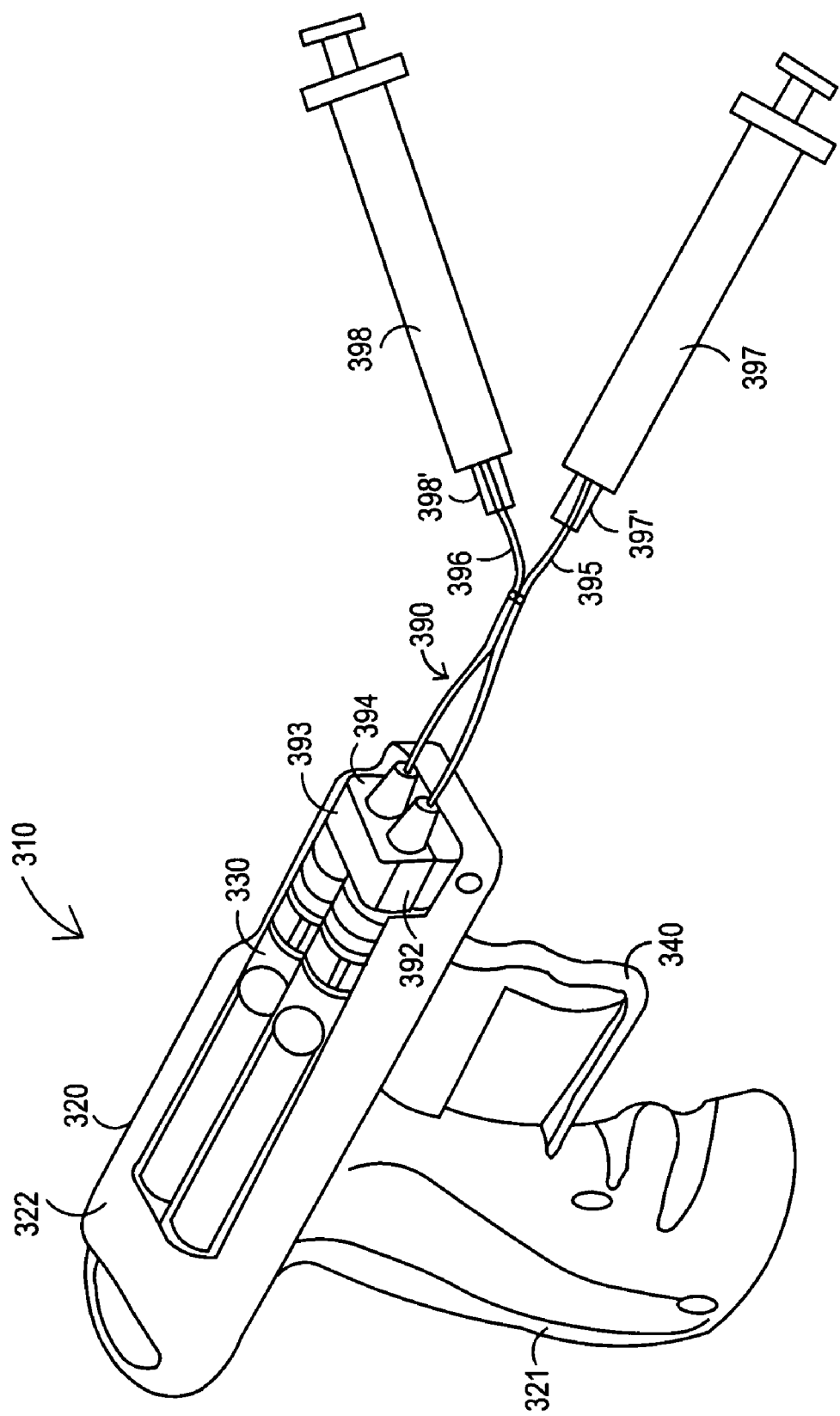
FIG. 11 shows the device of this invention with a fill manifold operably attached to the device.

Instead of the dispenser manifold 60, a fluid fill manifold 90 as depicted in FIG. 11 can be used to load fluids into the cylinders 31, 31' of the cartridge 30. Like the dispenser manifold 60, the fill manifold 90 includes inlet ports (not shown) that sealably align and couple with exit ports 38, 38'. The fill manifold 90 includes fittings 92, 93, and an optional hood 64. However, the fill manifold 90 includes tubes 95, 96 that couple to syringes 97, 98 that are filled with the fluids to be introduced into the cylinders 31, 31'. The syringes 97, 98 connect via luer fittings 99, 99' to the tubes. Thus during use the syringes 97, 98 are filled with fluids (e.g. a thrombin solution and a fibrinogen solution) to be introduced into the cylinders 31, 31'. The syringes are locked into place using the luer fittings, and then the fluids are injected into the cylinders at which time the plungers 36, 36' are driven back. Next, the fill manifold 90 is removed and replaced with the dispenser manifold 60, which also has fitting to lock the fill manifold in, after which time the surgeon primes the device for use, inserts and locks the inner needle within the outer needle, and injects the biologic sealant of choice into a desired location, such as a disc, in the body. Thus, the fill manifold for introducing fluids into the cylinder includes a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor. It should be appreciated that the fill manifold 90 can be alternatively connected to a wide variety of refilling parts other than the syringes 97, 98. Thus, the fluid fill manifold 90 can use, for example, pressurized containers, automated injection devices, fluid bags that are manually or automatically squeezed to effect refilling into the cylinders, fluid ampoules that are punctured with needles to access the fluids using pressurized gas to force the fluids into the cylinders, and so on.

Figure 8:
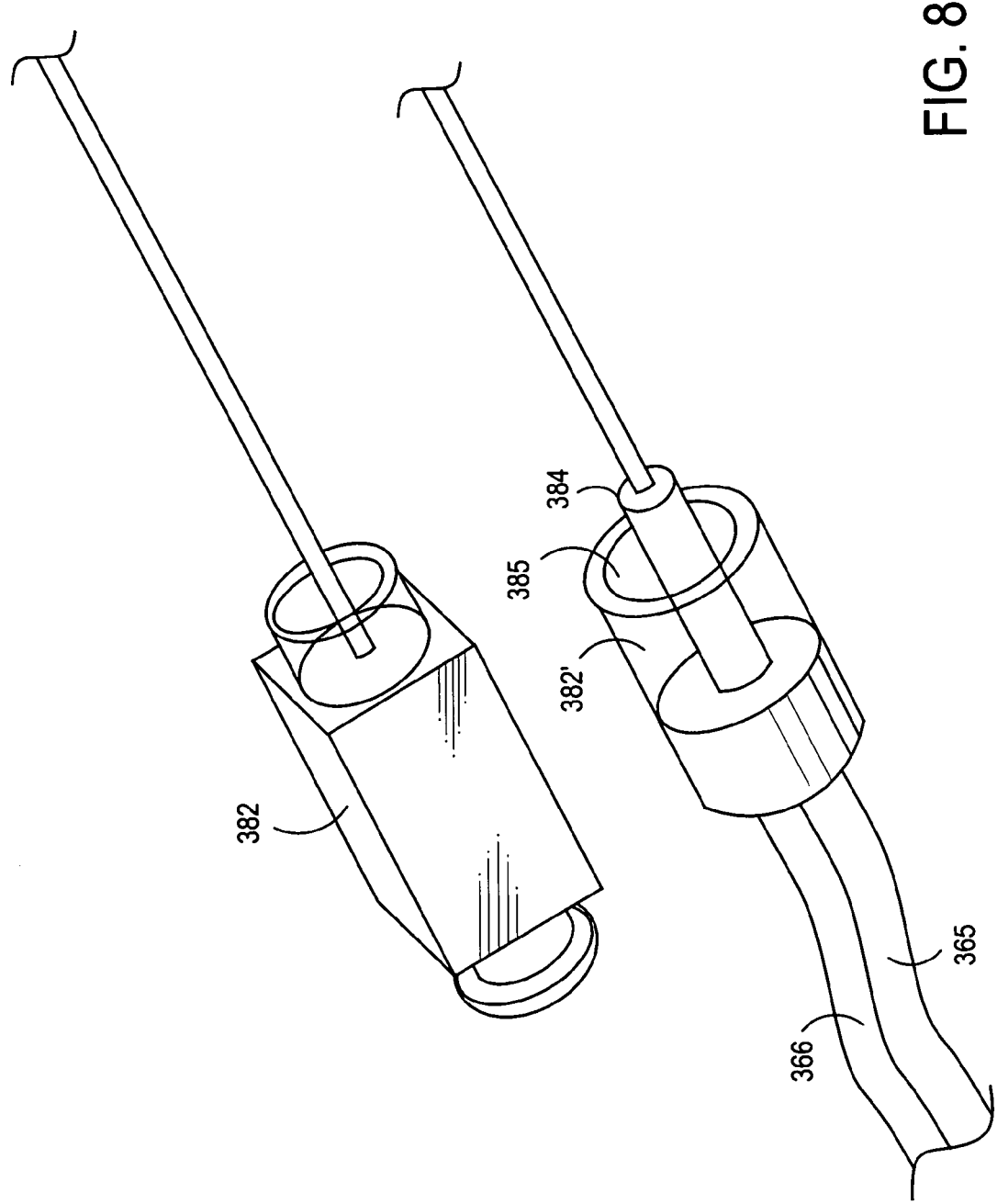

The needle assembly 80 is depicted in FIGS. 6-8. The needle assembly may include two coaxial needles, or an outer needle and an inner polymeric catheter. In FIG. 6, the outer needle 81, which is inserted directly into the patient to be treated, is connected via luer fittings 82, 82' with the outer needle 81 surrounding an inner needle 82 (see FIG. 7). The outer needle is typically an 18-22 gauge spinal needle that includes a bent portion 81' to assist the surgeon in navigating the body during insertion of the spinal needle. The inner needle can be of any size such that fluids may flow in the gap between the needles. In certain embodiments, the inner needle 83 may include ports near the tip 83' to facilitate potentially improved mixing of the fluids. Likewise, the tip 83' may be capped. FIGS. 9A-9C illustrate cross-sectional views of needles and catheters that may be employed in the practice of this invention. If a multi-lumen catheter or needle is employed, then the luer fitting would be adapted to delivery each fluid to a respective lumen. Referring again to FIGS. 6-8, the inner needle 83 can be of any length but typically is sized so that when the inner and outer needles are coupled together the tip 83' of the inner needle 83 extends to within between 1 mm and 50 mm of the tip 81' of the outer needle 81, in other embodiments is from about 0.5 inch to about 1.5 inch from the tip of the outer needle, and in one embodiment is from about ¾ inch to about 1 inch from the distal tip of the outer needle. In one embodiment, a fibrinogen solution is provided to the inner needle 83 while a thrombin solution is provided to the outer needle 81. Fluid mixing is initiated at the tip 83' of inner needle 83.

FIGS. 9A and 9B show representative cross-sectional views of multi-lumen catheters. FIG. 9A shows a bilumen catheter 200 wherein the lumen are in side-by-side arrangement and in which fibrinogen would be injected through lumen 201 and the activating compound through lumen 202. In FIG. 9B a trilumen catheter 210 is depicted wherein a first lumen 211 may carry one fluid, second lumen 212 carries a second fluid, and a third lumen 213 may carry and additive or have a wire inserted through the lumen 213 to improve the physical integrity and rigidity of a polymeric catheter. FIG. 9C depicts a trilumen catheter 230 wherein the lumen 231, 232, and 233 are arranged in sequence (in side-by-side relationship). A multi-lumen catheter can be used in this invention. A multi-lumen catheter can have a number of cross-sectional structures. The catheter can also have more than three lumen.

FIG. 8 shows a detailed embodiment of the luer fitting 82'. Thus, fibrinogen tube 65 feeds fibrinogen solution directly into a port 84 that couples to the inner needle 83. By contrast, tube 64 feeds thrombin solution, for example, into the hub (the void space) 85 of the luer fitting 82' whereby when the outer needle 81 is connected via luer fitting 82 the thrombin solution flows into the hub and into needle 81. The two fluids do not commingle until one of the solutions exits the inner needle 83.

Figure 12:
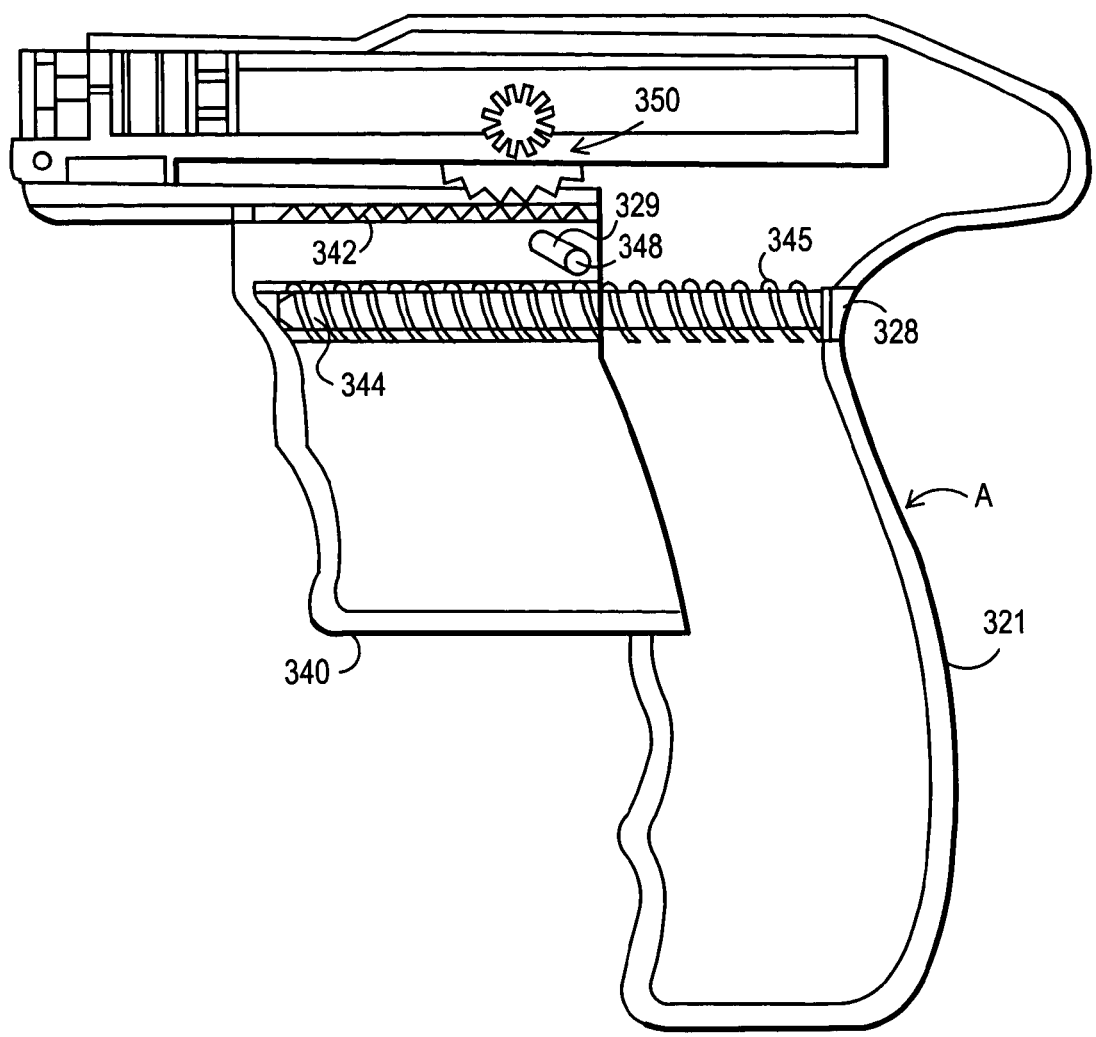
FIG. 12 shows the device of this invention from a cross-sectional view.

The trigger 40 is depicted in greater detail in FIG. 2. The trigger includes a toothed rack 42. Upon application of pressure by the surgeon to the trigger 40, the trigger 40 and rack 42 move backwards in the direction of the handle 21. The rack 42 then engages the wheel assembly 50, which rotates as the rack 42 moves backward. The wheel assembly 50 thereby drives rams 34, 34' which move plungers 36, 36' forward toward the exit ports 38, 38'. In one embodiment, the trigger is configured such that the teeth of rack 42 engage the teeth of the wheel assembly 50 when pressure is applied to the trigger 40, and configured such that the rack 42 drops away when pressure is released so that the respective teeth no longer engage. This configuration can be provided, for example, by adapting the housing 20 and trigger 40 such that the backward motion of the trigger raises the rack 42 such as, for example, in FIG. 12. In FIG. 12, the trigger 40 includes a guide bore 44 wherein a guide post 28 attached to the housing glides through the guide bore 44 upon application of pressure to the trigger 40. Upon release of pressure, spring 45 returns the trigger 40 to its original position. As the trigger 40 slides towards side A of the handle 21, a pin 48 that is mounted or integral with the rack 42 slides in the slot 29 to force the rack 42 up or down depending on the angle of the slot 29 to thereby engage the wheel assembly 50 as pressure is applied to the trigger 40. In this configuration, the slot 29 is a part of and integral with the housing 20. Alternatively, the rack 42 may include a slot with a pin being mounted within the housing 20, such that the pin glides in the slot to force the rack 42 to engage the wheel assembly 50.

The delivery device of this invention can be used to deliver a wide variety of biologic materials such as but not limited to fibrin sealant, synthetic polymers such as but not limited to polyvinylpyrrolidone, polyvinyl alcohol, polyacrylic acid, polyethoxazoline, polyhydroxyethyl acrylate, polyhydroxyethyl methacrylate, polysaccharides, polypeptides, polymers made from polyethylene glycol, materials disclosed in U.S. Pat. No. 6,428,576 (Haldimann) which is incorporated herein by reference, and so on, with or without additives. Fibrin sealant is preferred in the practice of this invention. Fibrin sealant comprises a fibrinogen component and a thrombin component that converts fibrinogen to fibrin. The sealant may contain one or more other components. The fibrin sealant is injected into, for example, the disc to seal fissures and tears in the annulus fibrosus. Defects in the annulus fibrosus are commonly diagnosed, currently, using MRI scans and discograms. This can treat both discogenic low back pain and radiculopathy leg pain when injected into the lumbar intervertebral disc.

The fibrinogen used in the practice of this invention includes any fibrinogen that will form fibrin in a human body. Fibrinogen is frequently available in freeze-dried form, and must be reconstituted prior to use. The fibrinogen can also be frozen or fresh. The fibrinogen can be autologous (from the patient to be treated), human including pooled human fibrinogen, recombinant, and bovine or other non-human source such as fish (e.g., salmon and sea trout). The fibrinogen is used in an amount suitable for the given treatment, patient, and so on. The freeze-dried fibrinogen can be reconstituted using, for example, saline, a saline solution containing aprotinin, a saline solution containing calcium chloride, a saline solution containing one or more other additives such as a local anesthetic, or a solution containing combinations of additives.

Thrombin is typically the enzyme used which serves to change fibrinogen to fibrin. However, other enzymes can be used such as those derived from snake venom (e.g., batroxobin), or spider venom as is known in the art. Thrombin is available commercially, typically in its freeze-dried form. Freeze-dried thrombin must be reconstituted prior to use. The thrombin can also be frozen or fresh. Thrombin can be autologous, from a human or pooled human supply, bovine, or other non-human source such as various arachnids and other venomous species. The thrombin is used in any amount which facilitates changing the fibrinogen to fibrin, as is known to one of skill in the art. The thrombin can be reconstituted using saline, a saline solution containing calcium chloride, a saline solution containing one or more other additives such as a local anesthetic, or a solution containing calcium chloride and one or more additives.

Additional additives may be added to the fibrin sealant such as, but not limited to: antibiotics; antiproliferative, cytotoxic, and antitumor drugs including chemotherapeutic drugs; analgesic; antiangiogen; antibody; antivirals; cytokines; colony stimulating factors; proteins; chemoattractants; EDTA; histamine; antihistamine; erythropoietin; antifungals; antiparasitic agents; non-corticosteroid anti-inflammatory agents; anticoagulants; anesthetics including local anesthetics such as lidocaine and bupivicaine; analgesics; oncology agents; cardiovascular drugs; vitamins and other nutritional supplements; hormones; glycoproteins; fibronectin; peptides including polypeptides and proteins; interferons; cartilage inducing factors; protease inhibitors; vasoconstrictors, vasodilators, demineralized bone or bone morphogenetic proteins; hormones; lipids; carbohydrates; proteoglycans such as aggrecan (chondrotin sulfate and deratin sulfate), versican, decorin, and biglycan; antiangiogenins; antigens; DBM; hyaluronic acid and salts and derivatives thereof; polysaccharides; cellulose compounds such as methyl cellulose, carboxymethyl cellulose, and hydroxy-propylmethyl cellulose and derivatives thereof; antibodies; gene therapy reagents; genetically altered cells, stem cells including mesenchymal stem cells with transforming growth factor, and/or other cells; cell growth factors to promote rehabilitation of damaged tissue and/or growth of new, healthy tissue such as BMP7 and BMP2; type II collagen; elastin; sulfated glycosaminoglycan (sGAG), glucosamine sulfate; pH modifiers; methylsulfonylmethane (MSM); osteogenic compounds; osteoconductive compounds; plasminogen; nucleotides; oligonucleotides; polynucleotides; polymers; osteogenic protein 1 (OP-1 including recombinant OP-1); LMP-1 (Lim Mineralization Protein-1); cartilage including autologous cartilage; oxygen-containing components; enzymes such as, for example, peroxidase, which mediate the release of oxygen from such components; melatonin; vitamins; and nutrients such as, for example, glucose. However, it is foreseeable that any of these additives may be added to the fibrin sealant separately or in combination. One or more of these additives can be injected with the fibrinogen and thrombin, or alternatively one or more of these components can be injected separately, either before or after the fibrin sealant has been injected. For solutions containing an incompletely water-soluble additive(s), an anti-caking agent such as, for example, polysorbate, may be added to facilitate suspension of this component. Glycol may be inappropriate for use as an anti-caking agent in the instant invention.

The biologic sealant including fibrinogen and thrombin (fibrin sealant) are injected in amounts effective to seal a given defect of the disc, as is apparent to one of skill in the art. The amount of thrombin can be varied to reduce or lengthen the time to complete fibrin formation. In general, the higher level of thrombin per unit amount of fibrinogen, the faster fibrin formation occurs. If slower fibrin formation is desired, then less thrombin is used per unit fibrinogen. The use of calcium chloride in one or both of the component solutions will affect the strength of the fibrin so formed, with increasing amount of calcium chloride increasing the strength of the fibrin clot. Generally, for a composition comprising fibrinogen that is an aqueous solution, it is believed that from about 3 mL to about 5 mL of such composition is sufficient to be an effective fibrin sealant. However, depending on the use of the composition, the dosage can range from about 0.05 mL to about 40 mL.

Fibrin sealants mimic the final stage of the natural clotting mechanism. Typically, such sealants entail the mixing of a fibrinogen component with an activating enzyme such as thrombin. Thrombin is an enzyme that exists in blood plasma which causes the clotting of blood by converting fibrinogen into fibrin. In normal practice, the components of the fibrin sealant are reconstituted separately, from a freeze-dried state, prior to use. However, the use of samples prepared from a frozen state or a fresh state is also acceptable. To increase biocompatibility of the sealant with host tissue, various components may be supplied endogenously from host body fluids. Combining the reconstituted components produces a viscous solution that quickly sets into an elastic coagulum. A method of preparing a conventional fibrin sealant is described by J. Rousou, et al. in Journal of Thoracic and Cardiovascular Surgery, vol. 97, no. 2, pp 194-203, February 1989. Cryoprecipitate derived from source plasma is washed, dissolved in buffer solution, filtered and freeze-dried. The freeze-dried fibrinogen is reconstituted in a fibrinolysis inhibitor solution containing, for example 3000 KIU/ml of aprotinin (a polyvalent protease inhibitor which prevents premature degradation of the formed fibrin). The solution is stirred and heated to a temperature of about 37° C. Each solution (the thrombin and fibrinogen solutions) is drawn up in a dual barrel syringe and mounted on a Y-connector to which a needle is attached for delivery of the combined solution. (See, e.g. the DUPLOJECT® device, from ImmunoAG, Vienna, Austria). Thus, mixing of the components only occurs during the delivery process which facilitates clot formation at the desired site of application only.

It should be appreciated that fibrin formation begins immediately on contact of the fibrinogen and thrombin. The term "injecting" of fibrin sealant or other biologic sealant thus encompasses any injection of components that form sealant in the disc, including circumstances where a portion of the components react to form sealant due to mixing prior to contact with or actual introduction into the disc (i.e., within the needle assembly).

It should also be appreciated that the point, or points, of injection (e.g., at the tip of a spinal needle) can be within the annulus fibrosus or in the nucleus pulposus. If the injection occurs in the nucleus pulposus, the injected components may form a patch at the interface between the nucleus pulposus and the annulus fibrosus, or, more commonly, the components flow into the defect(s) (e.g., fissures) of the annulus fibrosus and potentially "overflowing" into the interdiscal space. In practice, over-pressurizing the disc by injecting the components into the disc should be avoided.

In one embodiment, about 75-105 mg/mL of freeze-dried fibrinogen is reconstituted according to conventional methods, and about 45-55 mg/mL thrombin component is reconstituted separately from a freeze-dried state according to the methods and compositions of the present invention. Freeze-dried fibrinogen and freeze-dried thrombin are available in kit-form from such manufacturers as Baxter under names such as TISEEL®. These two fibrin sealant components can be prepared for example in about 2 mL samples each to yield approximately 4 mL of total sealant (reconstituted fibrinogen plus reconstituted thrombin).

While several methods and compositions may be used for preparing the freeze-dried thrombin for use in the invented fibrin sealant, one method is providing about 45-55 mg/mL of freeze-dried thrombin and mixing it with a reconstituting solution. The reconstituting solution may optionally further comprise about 0.1-100 milligrams of another additive described herein (e.g., local anesthetic) and/or calcium chloride. The calcium chloride concentration can be, for example, 1-100 millimoles/mL, and in one embodiment 4-40 millimoles/mL. If employed, the calcium chloride concentration should be sufficient to further the polymerization reaction that forms a durable fibrin sealant clot. A preservative-free reconstituting solution may be desirable, but is not required.

A contrast agent may be used in conjunction with the injection of the fibrin sealant. The contrast agent may be injected prior to injection of the fibrin sealant. Alternatively, the contrast agent is included in the fibrinogen component or thrombin component that is injected into the disc. Contrast agents and their use are well known to one of skill in the art.

Alternative amounts and concentrations of fibrinogen and thrombin may be used to form the desired fibrin sealant clot in the body. For example, as discussed above, varying the fibrinogen and/or thrombin amount/concentration may be done to vary the viscosity and the "setting time" of the combined fibrinogen and thrombin components. Likewise, varying fibrinogen may change the density of the combined components, which may be important for controlling flow through a long conduit such as a catheter into the body. Varying thrombin may vary the polymerization time of the components, which may be important for controlling the time at which the clot forms for ensuring the components set-up at the proper site and time in the body rather than setting-up prematurely.

When acquired in freeze-dried form, the thrombin and fibrinogen need to be reconstituted for use. The thrombin reconstituting solution (e.g., a saline based solution), optionally containing one or more additives, can be prepared in a single vial prior to mixing with the freeze-dried thrombin. This component of the fibrin sealant may then be provided to users in a reconstituted state, or in two uncombined vials containing freeze-dried thrombin and a premixed reconstitution solution. Mixing of the contents of the two vials may be performed at any point up to, and including, the time at which the fibrin sealant is injected into the patient. Reconstitution of the fibrinogen solution can be accomplished according to conventional methods. For example, the fibrinogen component may be reconstituted in an aprotinin saline solution which optionally contains additives such as, for example, a local anesthetic. If desired, the thrombin or the fibrinogen or both can be reconstituted using a saline solution that contains one or more additives. All solutions are brought to a temperature of about 37° C. Preferably, the thrombin is combined with the fibrinogen solution using the dual-syringe injection procedure described herein to form a single sealant composition which is injected into a patient. The instant invention provides a vehicle for the delivery of the sealant that conveys the sealant to the precise area of the back, seals any annular fissures, and holds the fibrin in place via the elastic coagulum. In addition, the biodegradable nature of the formed fibrin clot minimizes or eliminates the need for invasive surgical removal following the effective period of use. Therefore, an advantage of the sealant and method of application is the ability to provide a minimally invasive means of accomplishing localized, prolonged sealing of defects (e.g., fissures) in the annulus fibrosus, and if an additive is in the sealant, time-released additive delivery.

The fibrin sealant may be injected into the disc or other body area using procedures well known to one of skill in the art. In general, the fibrin sealant of this invention is injected into the disc, the epidural space, the zygaphysical (2-joint) joint, the vertebral canal, and/or thecal sac. With respect to an injection of fibrin sealant into a disc (an intra-discal injection) serves to create a fibrin matrix which seals the disc from leaking material from the nucleus into the area outside the disc. For example, the fibrin sealant can be delivered by fluoroscopic transforaminal lumber epidural or intra-discal injection, such as described in U.S. Pat. No. 6,468,527, incorporated herein by reference. For the treatment of back injuries such as these, the fibrin sealant is injected into the nucleus pulposus to fill any fissures or voids of the annulus fibrosus, to seal the bone end plates to the disc, increase pressure of the disc, and to increase the height of the disc space. The injection may also serve to coat areas adjacent to the disc, directly on the nerve roots and surrounding areas which serve to protect those areas from the effects of the leaking nucleus material. Sealing the fissures and bone end plates halts the leakage of harmful chemicals into the disc environment and prevents the initiation of foreign-body reactions towards the damaged disc by the immune system. Increasing the disc space relieves pressure from the nerve root. That is, as a result of the injection, an increase of the disc height occurs, which increases the spacing between lamina, and which in turn relieves pressure on the nerve roots on the lamina. For this application, supplementation of the fibrin sealant with growth factors may promote rehabilitation of the damaged tissues or the gradual replacement of the fibrin sealant with healthy tissue.

Use of the improved fibrin sealant composition may be better understood by reference to the following examples. These examples are representative and should not be construed to limit the scope of this invention or claims hereof. Unless otherwise indicated (example 3), corticosteroid is absent from the fibrin sealant being used in these examples and the procedures were conducted in the absence of a heating step of the nucleus fibrosus and annulus fibrosus.

Example 1

Fluoroscopic Transforaminal Epidural Injection

With a patient in the prone position on the imaging table, a fluoroscope is positioned and adjusted to locate the intervertebral foramen of the affected nerve root. A curved 22 ga.×3.5" needle is introduced after anesthetizing the skin and deep tissue. The needle is advanced under direct fluoroscopic vision to a position in the anterior epidural space. Positioning of the needle is verified by a lateral fluoroscopic view and by injecting contrast medium through the needle. Such positioning may or may not require further adjustment. If adjusted, location of the needle is once again verified. Advancement of the needle into the correct region may stimulate pain in a manner consistent with the initial complaint. Therefore, needle placement may also be verified by the patient's pain recognition. The epidural space is anesthetized with injectable anesthetic. The fibrin sealant of fibrinogen and thrombin (prior to clotting) is then introduced using the device of this invention such as shown in the FIGS. until the volumes of the dual syringe system are sufficiently depleted. The fibrin sealant then coats the nerve root and annulus and the needle is withdrawn. Patient observation and vital signs monitoring is performed for about 20-30 minutes following the procedure.

For this procedure, a sufficient volume of the fibrin sealant is injected to effectively hydro-dissect the area around the targeted nerve root. It is believed that due to the avascular nature of the epidural space, the absorption/degradation period is typically longer than that observed for open applications in regions with greater vascularity and exposure to room air at the time of application.

The ability of the fibrin sealant to seal annular fissures related to disc herniation offers a therapeutic benefit to patients. Chemical radiculitis, or inflammation of the nerve root, is known to be quite painful in some instances. It is believed that use of the fibrin sealant in the above described manner not only coats the nerve root, but also seals annular fissures surrounding the herniated disk. As a result of the hydro-dissection of the area around the affected nerve root, the sealant also seals annular fissures from outside the annulus.

Example 2

Fluoroscopic Guided Intra-Discal Injection

After sterile preparation, an introducer needle is advanced in oblique projection to a superior articular process. A curved spinal needle is advanced through the introducer needle into the disc. Both anterior-posterior and lateral fluoroscopic projections are used to confirm proper needle placement. If the needle placement needs to be adjusted, placement is again confirmed fluoroscopically. A contrast agent is injected to confirm needle placement. In patients with chemical radiculitis, the contrast agent can be observed to be leaking through the annular fissures and/or intra-discal pathology can be identified. Once the needle is properly positioned in the intra-discal space, the fibrin sealant is injected using the delivery device of this invention such as shown in the FIGS. The fibrin sealant is observed to force the contrast agent from the intra-discal space as it seals the annual fissures. Alternatively, the contrast agent is injected with the sealant. Alternatively, no contrast agent is used. The procedure seals the defects/fissures of the annulus fibrosus and stops the chemical leakage and facilitates regeneration within the disc.

Example 3

Comparative Assessment of the Physical Property of Clots

TISSEEL VH S/D fibrin sealant was prepared according to manufacturer guidelines. The reactive components were mixed and delivered using a DUPLOJECT delivery device or the deliver device of this invention as shown in FIGS. 1-8 and 9-12.

In the device of this invention used in this example, the tip of the inner needle was approximately one inch short of the distal tip of the introducer needle. The inner needle was a 22 gauge needle and the outer needle was an 18 gauge needle. As used herein including Table 1, "Biostat" refers to the device used in the tests constructed according to this invention.

A DUPLOJECT delivery device is the standard device used currently for mixing and providing fibrin sealant. The DUPLOJECT device includes dual syringes that feed fibrinogen solution and thrombin solution into a Y-connector where mixing of the solutions is initiated. The DUPLOJECT device is equipped with a standard one inch length 18 gauge needle, which is the needle provided with the DUPLOJECT delivery device. In use, solutions are placed in two syringes, the syringes are loaded into the dual syringe clip of the DUPLOJECT device, the mixing chamber is attached to the tips of the syringes and fastened to the dual syringe clip using the retaining strap, and the needle is then attached to the mixing chamber. The DUPLOJECT delivery device has been approved for use with fibrin sealant by the US Food and Drug Administration, and is mentioned in U.S. Pat. No. 6,468,527 for use in injecting fibrin sealant and corticosteroid into a disc.

Identical fibrinogen and thrombin solutions (TISSEEL fibrin sealant components using 500 IU/mL thrombin) were loaded into in each device. The solutions were then pushed through the devices so that fibrin sealant was injected from each device. A total of eight clots were cast from four batches of sealant for each delivery device. Controlled sample volumes (1.6 mL) were delivered by extrusion into controlled diameter test tubes (12×75 mm). This sample preparation protocol was designed to ensure the formation of a level, planar test surface with homogenous product distribution and controlled surface area and sample height. The test tubes were sealed and stored in a 37 degree Centigrade water bath for 90 minutes to allow complete product curing prior to mechanical testing. The mechanical properties of the resulting clots were measured, including failure load, elastic stiffness, and failure deformation. Material toughness was also estimated by calculating the area under the load-deformation curves.

A calibrated Texture Analyzer XT was used as a multifunction tensiometer to measure the forces generated during the controlled depression (2 mm/min, 10 mm maximum displacement) of a ¼ inch cylindrical probe into the surface of the clot. Compression of the gel yielded a steady linear rise in load until failure, demonstrated graphically by an abrupt deviation from linearity. As used herein, failure force refers to the force measured at the moment of the deviation from linearity. Failure displacement refers to the distance traveled by the probe until the moment of deviation, with failure deformation providing an estimate of the clot ductility. Elastic stiffness refers to the change in force over change in time (slope) of the linear portion of the load-deformation graph just preceding failure. Elastic stiffness provides and assessment of the clot's resistance to deformation, with higher values representing stiffer materials.

The following Table 1 provides the results of the mechanical testing of fibrin sealant clots produced by the DUPLOJECT device and the device according to this invention.

TABLE 1

| Property | DUPLOJECT N | DUPLOJECT Mean | DUPLOJECT SD | Biostat N | Biostat Mean | Biostat SD |
|---|---|---|---|---|---|---|
| Failure load (g) | 7* | 386 | 88 | 8 | 300 | 148 |
| Elastic Stiffness (g/mm) | 8 | 235 | 61 | 8 | 107 | 42 |
| Failure Deformation (mm) | 7* | 2.64 | 0.35 | 8 | 6.56 | 1.65 |
| Fracture toughness ($K_{1c}$) | 7* | 269.8 | 50.7 | 8 | 543.5 | 244.6 |

*One aberrant value removed based on Dean and Dixon outlier detection method. All outliers were from a single sample.

As shown in Table 1, the DUPLOJECT device and the Biostat device produced clots with average elastic stiffness loads of 235 g/mm (+/−61) and 107 g/mm (+/−42), respectively. The difference in elastic stiffness was statistically significant (t-test, p=0.0004). On average the clots produced from the Biostat device were reduced in elastic stiffness by 54% relative to the DUPLOJECT device.

The DUPLOJECT device and the Biostat device produced clots that failed after an average deformation of 2.64 mm (+/−0.35) and 6.56 mm (+/−1.65) respectively. The difference in failure deformation was statistically significant (t-test, p=0.0002). On average, surprisingly, the clots produced from the Biostat device withstood 165% more deformation prior to failure relative to the DUPLOJECT device.

The DUPLOJECT device and the Biostat device produced clots with an average material toughness proportional to 269.8 g-mm (+/−50.7) and 543.5 g-mm (+/−244.6, respectively. The difference in toughness was statistically significant (t-test, p=0.016). On average, surprisingly, the clots produced from the Biostat device could absorb twice as much energy (+101.5%) prior to catastrophic failure relative to the clots produced by the DUPLOJECT device.

These tests show that, unexpectedly, the device of this invention produces clots with significantly superior mechanical properties than clots made using a standard DUPLOJECT device.

In addition, proteolytic degradation resistance tests were conducted on additional fibrin samples. The procedures above were used to prepare clots from the DUPLOJECT device and Biostat device. It was found, surprisingly, that clots made using the Biostat device had increased resistance to fibrinolytic degradation relative to clots made using the DUPLOJECT device.

Viscometry profiles were also determined. The procedures above were used to prepare clots from the DUPLOJECT device and Biostat device. Reheometric Scientific's SR5 Controlled Stress Rheometer was used to measure the rheological properties of the setting fibrin clots at body temperature. A cone and plate geometric configuration (d~25 mm, 4°) was used for viscosity profile assessment. Standardized test protocols were utilized. Shear rates ranging from 0.1 to 80 $\sec^{-1}$ were used. In the dynamic experiments, an oscillatory shear was applied to the samples while the corresponding elastic (G') and viscous (G") moduli were measured as a function of frequency. Samples were assessed using frequency ranges from 0.01 rad/s to 100 rad/s.

Figure 13:
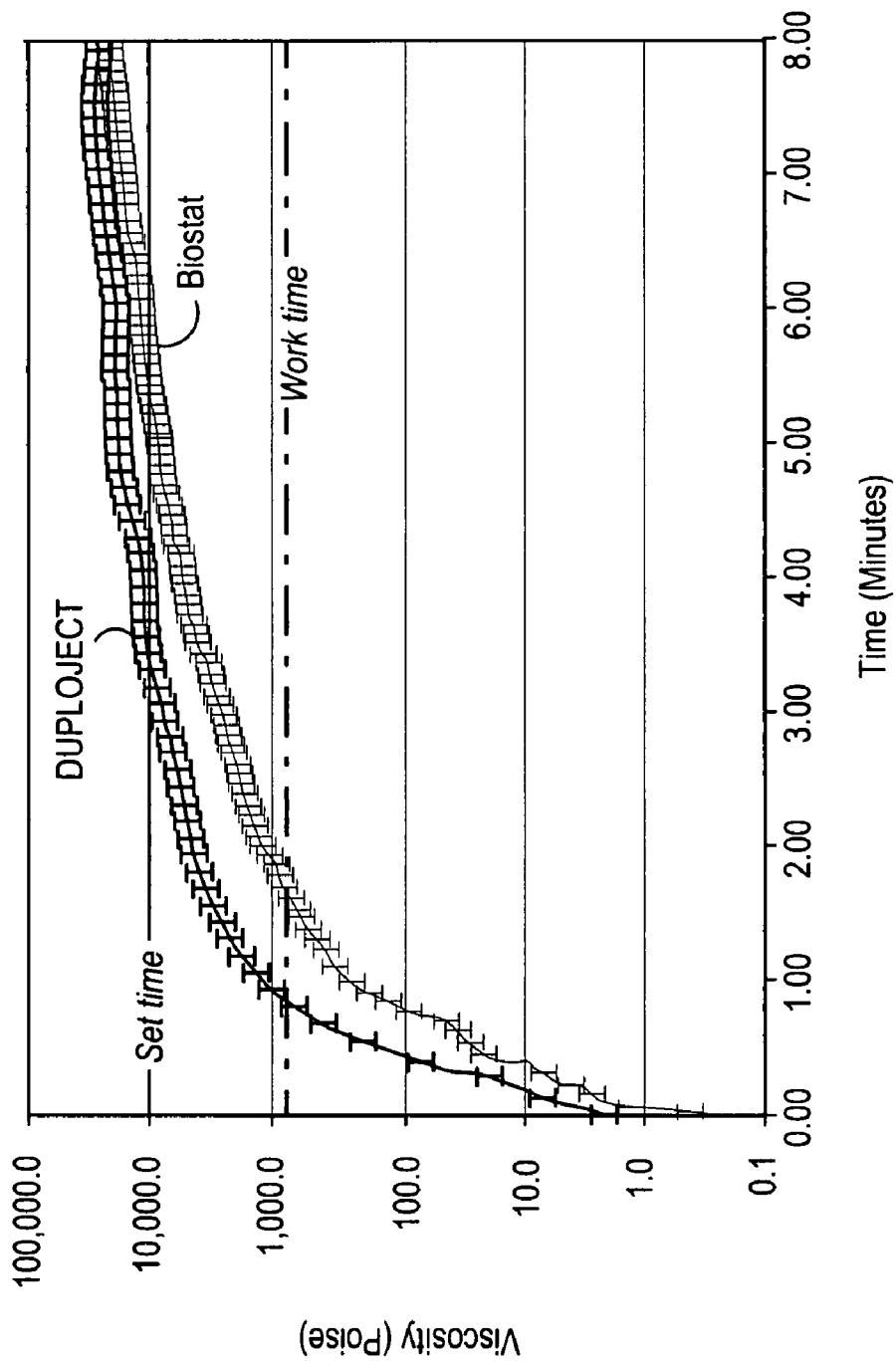
FIG. 13 shows a graph of dynamic setting viscosity profiles for fibrin delivered from a DUPLOJECT device and from a device of this invention.

For purposes of this example, working time refers to the duration required for the fibrin solution viscosity to reach 750 poise. At this viscosity, the pressure required for syringe delivery exceeds a 15 psi threshold for hand delivery. The working time limit represents the period of time the physician has to deliver the entire product to the disc. The data shows that the Biostat device increases working time significantly and provides significantly improved control for intradiscal delivery. In addition, the Biostat device provides fibrin sealant that allows for slow delivery and maximizes the potential for low viscosity components to permeate into annular disruptions (fissures). In particular, the Biostat device surprisingly increases work time to 1.75 minute (+/−0.73), an 134% average improvement over fibrin sealant made using the DUPLOJECT device which had a work time of 0.65 min (+/−0.02). The results are shown in FIG. 13. In FIG. 13 it can be seen that the fibrin sealant delivered from a DUPLOJECT device sets up significantly faster than fibrin sealant delivered from a Biostat device.

Likewise, the setting or solidification time was arbitrarily defined as the duration required for the fibrin solution viscosity to reach 10,000 poise (roughly equivalent to solid vegetable shortening). The results show that the Biostat device significantly and surprisingly increased the set time to 5.77 min (+/−1.76) from the 2.90 min (+/−0.38) from the DUPLOJECT device. This provides a distinct advantage for the practitioner by allowing the fibrin to more fully infiltrate annular fissures and so on, and associated significant performance benefits for intradiscal injection of a biologic sealant.

It is envisioned that the present invention may be used to address various conditions through use of the device of this invention in a manner similar to that described in the examples above. Discussion of this invention referenced particular means, materials and embodiments elaborating limited application of the claimed invention. The invention is not limited to these particulars and applies to all equivalents. Although this invention has been described above with reference to particular means, materials and embodiments, it is to be understood that the invention is not limited to these disclosed particulars, but extends instead to all equivalents within the scope of the following claims.

What is claimed is:

1. A device for delivery of biologic materials, comprising:
    a cartridge having at least two cylinder bores for fluids of the biologic materials to be delivered, wherein each cylinder includes an exit port for a fluid, a plunger within each cylinder for pushing the fluids out of the cylinder, a delivery manifold that operably connects to the exit ports of the cartridge, wherein the manifold connects to an inner hypodermic needle, a housing adapted to receive the cartridge, wherein the housing or cartridge includes an adaptor to receive and lock the manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

2. The device of claim 1, wherein the cartridge is a separate component from the housing that is inserted into the housing.

3. The device of claim 1, further comprising a pressure monometer operably connected to measure the pressure in at least one cylinder.

4. The device of claim 1, wherein the plungers are attached to the rams.

5. The device of claim 1, wherein the wheel assembly includes an inner toothed wheel sandwiched between two outer toothed wheels each of smaller diameter than the inner wheel.

6. The device of claim 1, wherein the drive rack engages the wheel assembly upon manual pressure to the trigger and wherein the drive rack disengages the wheel assembly upon release of pressure on the trigger, and falls away.

7. The device of claim 1, further comprising a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor.

8. The device of claim 1, wherein the delivery manifold comprises a delivery adaptor that includes at least two exit ports that each couple to the at least two exit ports of the adaptor, at least two conduits having two ends wherein a first end of each of the conduits connects to an exit port of the delivery manifold, and wherein a second end of each of the conduits connects to a dual port luer fitting, wherein the luer fitting is configured to deliver fluid from one conduit to the inner hypodermic needle and wherein the luer fitting is configured to deliver fluid from the second conduit to a space defined by the exterior of the inner needle and by a second larger diameter hypodermic needle that connects to the luer fitting with the inner hypodermic needle being within the inside of the second larger diameter hypodermic needle.

9. The device of claim 8, wherein the device includes the inner hypodermic needle and the second larger diameter hypodermic needle that are coupled to the luer fitting, and wherein the inner hypodermic needle does not extend past a distal tip of the second larger diameter hypodermic needle.

10. A method of making a device for delivery of biologic materials, comprising:

providing a cartridge having at least two cylinder bores for fluids to be delivered, wherein each cylinder includes an exit port for a fluid, providing a plunger within each cylinder for pushing the fluids out of the cylinder, providing a delivery manifold that operably connects to the exit ports of the cartridge, wherein the manifold connects to an inner hypodermic needle, providing a housing adapted to receive the cartridge, wherein the housing or cartridge includes an adaptor to receive and lock the manifold that operably connects to the exit ports of the cartridge, providing at least two toothed rams, wherein each toothed ram is at least partially within a cylinder bore, providing a trigger connected to the housing, wherein the trigger includes a toothed drive rack, providing a toothed wheel assembly that cooperates with the toothed drive rack and with the toothed rams.

11. The method of claim 10, wherein the housing and the cartridge are together monolithic.

12. The method of claim 10, wherein the cartridge is a separate component from the housing that is inserted into the housing.

13. The method of claim 10, further comprising providing a pressure monometer operably connected to measure the pressure in at least one cylinder.

14. The method of claim 10, wherein the plungers are attached to the rams.

15. The method of claim 10, wherein the wheel assembly includes an inner toothed wheel sandwiched between two outer toothed wheels each of smaller diameter than the inner wheel.

16. The method of claim 10, wherein the drive rack engages the wheel assembly upon manual pressure to the trigger and wherein the drive rack disengages the wheel assembly upon release of pressure on the trigger, and falls away.

17. The method of claim 10, further comprising providing a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor.

18. The method of claim 10, wherein the delivery manifold comprises a delivery adaptor that includes at least two exit ports that each couple to the at least two exit ports of the adaptor, at least two conduits having two ends wherein a first end of each of the conduits connects to an exit port of the delivery manifold, and wherein a second end of each of the conduits connects to a duel port luer fittings, wherein the luer fitting is configured to deliver fluid from one conduit to inner hypodermic needle and wherein the luer fitting is configured to deliver fluid from the second conduit to a space defined by the exterior of the inner hypodermic needle and by a second larger diameter hypodermic needle that connects to the luer fitting with the inner hypodermic needle being within the insider of the larger diameter hypodermic needle.

19. The method of claim 10, wherein the inner needle does not extend past a distal tip of the second needle.

20. A kit for treating a disc, comprising: fibrinogen, thrombin, and a device for delivery of biologic materials, wherein the device comprises:

a cartridge having at least two cylinder bores for the biologic materials to be delivered, wherein each cylinder includes an exit port for a fluid, a delivery manifold that operably connects to the exit ports of the cartridge, wherein the manifold connects to an inner hypodermic needle, a plunger within each cylinder for pushing the fluids out of the cylinder, a housing adapted to receive the cartridge, wherein the housing or cartridge includes an adaptor to receive and lock a manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

21. The kit of claim 20, the cartridge is a separate component from the housing that is inserted into the housing, wherein the kit further comprises a pressure monometer operably connected to measure the pressure in at least one cylinder; wherein the plungers are attached to the rams; wherein the wheel assembly includes an inner toothed wheel sandwiched between two outer toothed wheels each of smaller diameter than the inner wheel; wherein the drive rack engages the wheel assembly upon manual pressure to the trigger and wherein the drive rack disengages the wheel assembly upon release of pressure on the trigger, and falls away; wherein the kit further comprises a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor; wherein the kit further comprises a delivery manifold for delivering the fluids, comprising a delivery adaptor that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to deliver fluid from one conduit to an inner hypodermic needle and wherein the luer fitting is configured to deliver fluid from the second conduit to a space defined by the exterior of the inner hypodermic needle and by a second larger diameter hypodermic needle that connects to the luer fitting with the inner hypodermic needle being within the insider of the larger diameter hypodermic needle; and wherein the inner hypodermic needle does not extend past a distal tip of the second hypodermic needle.

22. A method of making a kit, comprising providing fibrinogen, providing thrombin, and providing a device for delivery of biologic materials, wherein the device comprises:

a cartridge having at least two cylinder bores for fluids of the biologic materials to be delivered, wherein each cylinder includes an exit port for a fluid, a plunger within each cylinder for pushing the fluids out of the cylinder, a delivery manifold that operably connects to the exit ports of the cartridge, wherein the manifold is coupled to an inner hypodermic needle, a housing adapted to receive the cartridge, wherein the housing or cartridge includes an adaptor to receive and lock the manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

23. The method of claim 22, wherein the cartridge is a separate component from the housing that is inserted into the housing further comprising providing a pressure monometer operably connected to measure the pressure in at least one cylinder; wherein the plungers are attached to the rams; wherein the wheel assembly includes an inner toothed wheel sandwiched between two outer toothed wheels each of smaller diameter than the inner wheel; wherein the drive rack engages the wheel assembly upon manual pressure to the trigger and wherein the drive rack disengages the wheel assembly upon release of pressure on the trigger, and falls away; further comprising providing a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor; further comprising providing a delivery manifold for delivering the fluids, comprising a delivery adaptor that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to delivery fluid from one conduit to an inner hypodermic needle and wherein the luer fitting is configured to delivery fluid from the second conduit to a space defined by the exterior of the inner hypodermic needle and by a second larger diameter hypodermic needle that connects to the luer fitting with the inner hypodermic needle being within the insider of the larger diameter hypodermic needle; and wherein the inner hypodermic needle does not extend past a distal tip of the second hypodermic needle.

24. A method of treating a disc that is leaking nucleus pulposus through at least one defect in the annulus fibrosus, comprising: injecting a fibrin sealant into the disc to reduce at least a portion of the at least one defect, wherein the fibrin sealant injected into the disc comprises fibrinogen and thrombin, wherein the fibrin sealant is injected using a delivery device that comprises:

a cartridge having at least two cylinder bores for fluids of the biologic materials to be delivered, wherein each cylinder includes an exit port for a fluid, a plunger within each cylinder for pushing the fluids out of the cylinder, a delivery manifold that operably connects to the exit ports of the cartridge, wherein the manifold connects to an inner hypodermic needle, a housing adapted to receive the cartridge, wherein the housing or cartridge includes an adaptor to receive and lock the manifold that operably connects to the exit ports of the cartridge, at least two toothed rams, wherein each toothed ram is at least partially within a cylinder bore, a trigger connected to the housing, wherein the trigger includes a toothed drive rack, a toothed wheel assembly that cooperates with the toothed drive rack and with the toothed rams.

25. The method of claim 24, wherein the cartridge is a separate component from the housing that is inserted into the housing; further comprising providing a pressure monometer operably connected to measure the pressure in at least one cylinder; wherein the plungers are attached to the rams; wherein the wheel assembly includes an inner toothed wheel sandwiched between two outer toothed wheels each of smaller diameter than the inner wheel; wherein the drive rack engages the wheel assembly upon manual pressure to the trigger and wherein the drive rack disengages the wheel assembly upon release of pressure on the trigger, and falls away; further comprising providing a fill manifold for introducing fluids into the cylinder, wherein the fill manifold comprises a fill manifold adaptor that couples to the adaptor of the delivery device wherein the adaptor includes at least two exit ports that each couple to the at least two exit ports of the housing adaptor, at least two syringes, at least two conduits wherein one end of the conduit connects to the syringe and a second end of the conduit connects to an exit port of the fill manifold adaptor; further comprising providing a delivery manifold for delivering the fluids, comprising a delivery adaptor that includes at least two exit ports that each couple to the at least two exit ports of the housing adaptor, at least two conduits having two ends wherein a first end of each of the conduits connects to an exit port of the delivery manifold, and wherein a second end of each of the conduits connects to a duel port luer fittings, wherein the luer fitting is configured to delivery fluid from one conduit to the inner hypodermic needle and wherein the luer fitting is configured to delivery fluid from the second conduit to a space defined by the exterior of the inner hypodermic needle and by a second larger diameter hypodermic needle that connects to the luer fitting with the inner hypodermic needle being within the insider of the larger diameter hypodermic needle; and wherein the inner hypodermic needle does not extend past a distal tip of the second hypodermic needle.

26. The device of claim 1, wherein a flexible tube is connected between the manifold and the inner hypodermic needle.

27. The device of claim 1, the at least two cylinder bores defines a first cylinder bore and a second cylinder bore, wherein the device includes an outer hypodermic needle that fits over the inner hypodermic needle when assembled, wherein first and second flexible tubes operable couple the inner hypodermic needle and the outer hypodermic needle to, respectively, the first cylinder bore and the second cylinder bore via the delivery manifold.

* * * * *